United States Patent [19]

Stiefel

[11] Patent Number: 4,843,096
[45] Date of Patent: Jun. 27, 1989

[54] TREATMENT OF ACNE

[75] Inventor: Werner K. Stiefel, Coral Gables, Fla.

[73] Assignee: Stiefel Laboratories, Inc., Coral Gables, Fla.

[21] Appl. No.: 935,603

[22] Filed: Dec. 1, 1986

Related U.S. Application Data

[63] Continuation of Ser. No. 748,913, Jun. 26, 1985, abandoned.

[51] Int. Cl.$^4$ ............................................. A61K 31/20
[52] U.S. Cl. .................................... 514/559; 514/725; 514/859
[58] Field of Search ........................ 514/559, 725, 859

[56] References Cited

U.S. PATENT DOCUMENTS

| | | | |
|---|---|---|---|
| 2,917,523 | 12/1959 | Pommer et al. | 260/410.9 |
| 3,143,564 | 8/1964 | Matsui et al. | 260/468 |
| 3,729,568 | 4/1973 | Kligman | 424/318 |
| 3,781,314 | 12/1973 | Bollag et al. | 260/410.9 |
| 3,882,244 | 5/1975 | Lee | 424/318 |
| 3,906,108 | 9/1975 | Felty | 424/318 |
| 3,931,257 | 1/1976 | Pawson | 260/408 |
| 3,932,665 | 1/1976 | Van Scott et al. | 424/333 |
| 3,950,418 | 4/1976 | Bollag et al. | 260/557 |
| 3,984,440 | 10/1976 | Bollag et al. | 260/345.2 |
| 3,984,544 | 10/1976 | Casmer | 424/243 |
| 4,021,574 | 5/1977 | Bollag et al. | 424/324 |
| 4,026,778 | 5/1977 | Lalonde et al. | 204/159 |
| 4,054,589 | 10/1977 | Bollag et al. | 260/408 |
| 4,105,681 | 8/1978 | Bollag et al. | 260/404 |
| 4,169,103 | 9/1976 | Haenni | 260/413 |
| 4,200,647 | 4/1980 | Bollag et al. | 424/305 |
| 4,225,527 | 7/1980 | Bollag et al. | 260/408 |
| 4,304,787 | 12/1981 | Gander et al. | 424/305 |
| 4,322,438 | 3/1982 | Peck | 424/318 |
| 4,333,924 | 6/1982 | Bowley et al. | 424/170 |
| 4,464,394 | 8/1984 | Bollag | 424/317 |
| 4,487,782 | 12/1984 | Mezick | 424/317 |

FOREIGN PATENT DOCUMENTS

| | | |
|---|---|---|
| 967484 | 5/1975 | Canada. |
| 1335867 | 10/1973 | United Kingdom. |
| 1676717 | 6/1977 | United Kingdom. |
| 1489133 | 10/1977 | United Kingdom. |

OTHER PUBLICATIONS

Cullen, Cutis, vol. 10, Dec. 1972, pp. 7T 1–3.
Pedace et al., "Topical Retinoic Acid in Acne Vulgaris," Br. J. Derm. (1971) 84, 465–469.
Verma et al., "Inhibition of 12-O-tetradecanoylphorbol-13-acetate-induced etc.," Cancer Research, 38, 793–801 (1978).
Elias et al., "Retinoids, Cancer, and the Skin," Arch. Dermatol., 117, 160–180 (1981).
Hixson et al., "Comparative Subacute Toxicity of all-trans- and 13-cis Retinoic Acid in Swiss Mice"; Toxicol. App. Pharmacol., 44, 29–40 (1978).
Bollag et al., "From Vitamin A to Retinoids etc." Annals N.Y. Acad. Sciences, (Feb. 27, 1981) 9–23.
Zile et al., "Identification of 13-cis retinoic acid in tissue extracts etc.", Biochim. Biophy. Acta., 141 (1967) 639–641.
Spearman et al. "Biological comparison of isomers and chemical forms of vitamin A", Brit. J. Derm. (1974) 90, 553–560.
Jarret, "The Action of Vitamin A on the Skin of Mammals", Acta Dermatovenes (Stockholm) Supple. 74, 73–75 (1975).
Zacharaiac, "Topical Vitamin–A–Acid in Acne", Acta Dermatovener (Stockholm), Suppl. 89 65–70 (1980).
Gomez et al. "Effect of 13-cis Retinoic Acid on the Hamster Flank Organ", J. Invest. Dermatol. 74, 392–397 (1980).
Plewig et al. "Effects of Two Retinoids etc.", Retinoids (Springer-Verlag) Orfanos, Ed., 219–235 (1981).
Abstracts, International Dermatology Symposium, Berlin 1980.
Mezick et al., J. Investigative Dermatology, 78(4) 350.
Mezick et al., J. Investigative Dermatology 83, 110–113 (1984).
Aston et al., J. Investigative Dermatology 82(6) 632–635 (1984).
Plewig et al., J. Investigative Dermatology 80(4) 357 (1983).
The Retinoids, vol. 2, Chapter 16, pp. 391–411, Academic Press (1984).

Primary Examiner—Leonard Schenkman
Attorney, Agent, or Firm—Bruce M. Collins

[57] ABSTRACT

Inflammatory acne is treated topically with a non-aqueous gel of 13-cis retinoic acid.

3 Claims, No Drawings

TREATMENT OF ACNE

CROSS REFERENCE TO RELATED APPLICATIONS

This is a continuation of Ser. No. 748,913, filed June 26, 1985, now abandoned.

DETAILED DESCRIPTION

The present invention pertains to the treatment of acne vulgaris, particularly in the inflammatory phase, in humans through the topical application of a non-aqueous gel composition comprising 13-cis retinoic acid.

The 13-cis retinoic acid will be present in an amount of from about 0.025 to about 0.1%, preferably 0.05%, by weight of the composition. The gel vehicle is a combination of ethanol and a cellulose, preferably hydroxypropyl cellulose, wherein the ratio of ethanol to the cellulose is approximately 32:1. A minor amount of an antioxidant such as butylated hydroxytoluene can be added.

A typical 0.05% non-aqueous gel formulation (with a 5% overage) is as follows:

| | | |
|---|---|---|
| 13-Cis Retinoic Acid | 0.0525 | parts by weight |
| Hydroxypropyl cellulose | 3.0000 | parts by weight |
| Ethanol (SDA-40B) | 96.8975 | parts by weight |
| Butylated hydroxytoluene | 0.0500 | parts by weight |
| Total | 100.0000 | parts by weight |

These materials are blended into a gel of high stability when stored below 30° C. (86° F.). Compositions containing 0.025% and 0.1% 13-cis retinoic acid are similarly prepared.

The compositions preferably are applied once or twice daily to acne lesions, utilizing a sufficient quantity of the composition to cover the affected area.

Study 1

21 Day Cumulative Irritancy

Sixteen human subjects entered and completed a double-blind, 21 day cumulative irritancy study of alcohol gels containing 13-cis retinoic acid, (0.025, 0.05, or 0.1%), retinoic acid (0.025, 0.05, or 0.1%), or a placebo gel. No adverse experiences occurred. Topical application of all 13-cis retinoic acid gels (0.025, 0.05, and 0.1%) and the placebo gel resulted in significantly (P=0.01) lower cumulative irritancy scores than the retinoic acid gel (0.025%).

Study 2

Dose Response Evaluation of Topical 13-Cis Retinoic Acid Gel in Acne Vulgaris A total of sixty patients with acne vulgaris entered a controlled, double-blind study comparing once daily treatment with 13-cis retinoic acid (0.025, 0.05, or 0.1%) topical gels to the vehicle gel (placebo). At the conclusion of a 12-week trial, there remained 13 patients in the 0.1% group, 9 patients in the 0.05% group, 14 patients in the 0.025 group, and 14 patients in the vehicle group.

Only mild, transient erythema and/or peeling were noted in some patients. No adverse experiences occurred. Twelve week treatment with 0.05% gel resulted in a 62% reduction in inflammatory lesions, a 48% reduction in non-inflammatory lesions, and a 2.4 acne severity grade reduction. The other treatments were substantially less effective. The acne severity grade reduction seen in the 0.05% group was significantly greater than in the vehicle group after 2, 6, 8, 10 and 12 weeks of therapy.

Study 3

Dose Response Evaluation of Topical 13-Cis Retinoic Acid Gel in Acne Vulgaris A total of sixty-nine patients with acne vulgaris entered a double-blind, controlled study utilizing twice daily treatment with 0.05% and 0.1% topical 13-cis retinoic acid gels as compared with a vehicle gel. At the conclusion of the 12-week trial, there remained 22 patients in the 0.1% group, 19 patients in the 0.05% group, and 22 patients in the vehicle group.

Mild to moderate erythema and/or peeling were noted in most patients. One patient in each of the 0.1% and 0.05% groups dropped out due to irritation. Reductions in inflammatory lesion counts (29 and 20%), non-inflammatory lesion counts (17 and 20%), and acne severity grade (1.3 and 0.6) were observed after 12 week therapy with 0.05% and 0.1% topical gels, respectively. Vehicle treatment increased both inflammatory (3%) and non-inflammatory (15%) lesion counts and had no effect on acne severity grade. The reductions in inflammatory lesion count and the acne severity grade in the 0.05% group were significantly greater than in the vehicle group after 8, 10 and 12 weeks of therapy. Treatment with 0.1% gel resulted in significantly greater reduction in inflammatory lesions and acne severity grade after 12 weeks of therapy.

Study 4

Safety and Efficacy of 0.05% 13-cis retinoic acid Topical Gel in the Treatment of Acne Vulgaris A total of ninety-four patients with acne vulgaris entered a double-blind, controlled study comparing twice daily treatment with 13-cis retinoic acid 0.05% topical gel as compared with the vehicle gel. At the conclusion of the 14-week trial, there remained 43 patients in the 0.05% group and 46 patients in the vehicle group.

Erythema and/or peeling was absent or mild in most patients. No patient dropped out due to adverse experience. Reductions in inflammatory lesion counts (60 and 27%), non-inflammatory lesion counts (51 and 18%), and acne severity grade (1.9 and 0.8) were observed after 14-week therapy with 0.05% topical gel and vehicle gel, respectively. Treatment with 0.05% gel resulted in a significantly greater reduction in non-inflammatory lesions and acne severity grade than vehicle treated patients at 5, 8, 11 and 14 weeks. The inflammatory lesion reduction seen in the 0.05% group was significantly greater than in the vehicle group after 8, 11 and 14 weeks of therapy.

Study 5

Safety and Efficacy of 0.05% 13-cis retinoic acid Topical Gel in the Treatment of Acne Vulgaris A total of sixty patients with acne vulgaris entered a double-blind, controlled study comparing twice daily treatment with 0.05% 13-cis retinoic acid topical gel to the vehicle gel. At the conclusion of the 14-week trial, there remained 28 patients in the 0.05% group and 29 patients in the vehicle group.

Erythema and/or peeling was absent or mild in most patients. No patient dropped out due to adverse experience. Reductions in inflammatory lesion counts (75 and 59%), non-inflammatory lesion counts (54 and 30%), and acne severity grade (2.1 and 1.8) were observed after 14-week therapy with 0.05% topical gel and vehicle gel, respectively. Treatment with 0.05% gel tended to reduce non-inflammatory lesions and acne severity and significantly reduced inflammatory lesions greater than vehicle group after 14 weeks of therapy.

Study 6

Safety and Efficacy of 0.05% 13-cis retinoic acid Topical Gel in the Treatment of Acne Vulgaris A total of fifty-eight patients with acne vulgaris entered a double-blind, controlled study comparing twice daily treatment with 0.05% 13-cis retinoic acid topical gel to the vehicle gel. At the conclusion of this 12-week trial, there remained 22 patients in the 0.05% group and 21 patients in the vehicle group.

Erythema and/or peeling was mild or moderate in most patients. Two patients, one in each group, dropped out due to irritation. Reductions in inflammatory lesion counts (63 and 24%), non-inflammatory lesion counts (63 and 12%), and acne severity grade (1.4 and 0.4) were observed after 12-week therapy with 0.05% topical gel and vehicle gel, respectively. Treatment with 0.05% gel resulted in a significantly greater reduction in inflammatory lesions, non-inflammatory lesions, and acne severity grade than vehicle group at 8 and 12 weeks of therapy.

Study 7

Safety and Efficacy of 0.05% 13-cis retinoic acid Topical Gel in the Treatment of Acne Vulgaris A total of fifty-five patients with acne vulgaris entered a double-blind, controlled study comparing twice daily treatment with 0.05% 13-cis retinoic acid topical gel to the vehicle gel. At the conclusion of this 12-week trial, there remained 18 patients in the 0.05% group and 20 patients in the vehicle group.

Erythema and/or peeling was absent or mild in most patients. No patients dropped out due to irritation. Reductions in inflammatory lesion counts (41 and 26%), non-inflammatory lesion counts (60 and 51%), and acne severity grade (0.7 and 0.6) were observed after 12 weeks of therapy with the 0.05% topical gel and vehicle gel, respectively. These differences in treatment response were not statistically significant but a trend for more favorable efficacy was observed with with 0.05% topical gel therapy in all three measured acne parameters.

Study 8

Photo-toxicity

A total of ten subjects entered and completed a photo-toxicity study of 0.05% 13-cis retinoic acid topical gel and its vehicle. No indication of photo-toxicity was noted in any of the ten subjects.

Study 9

Photocontact Allergy

A total of twenty-eight subjects entered a photocontact allergy study of 0.05% 13-cis retinoic acid topical gel and its vehicle. One subject dropped out for a reason unrelated to the test medications. No adverse experiences occurred. Some irritation occurred during the induction phase of the study but not during the elicitation phase. No indication of photocontact allergenicity was noted in any of the twenty-seven subjects who completed the entire study.

Study 10

Sensitization

A total of one hundred fifty-five subjects entered a repeated insult patch test of 0.05% 13-cis retinoic acid topical gel and its vehicle. One subject did not return after initial patching. No adverse experiences occurred. No indication of sensitization or irritation was noted in the 154 subjects who completed the entire test.

What is claimed is:

1. The method of treating inflammatory acne in a human which comprises topically applying an effective amount of a substantially non-aqueous gel composition comprising from about 0.025 to about 0.1% by weight of 13-cis retinoic acid.

2. The method according to claim 1 wherein the concentration of 13-cis retinoic acid is about 0.05%.

3. The method according to claim 2 wherein the gel vehicle is ethanol and hydroxypropyl cellulose in a weight ratio of approximately 32:1, respectively.

* * * * *